US009187401B2

(12) United States Patent
Hashmi et al.

(10) Patent No.: US 9,187,401 B2
(45) Date of Patent: Nov. 17, 2015

(54) PROCESS FOR PREPARING ALKOXY ARYL ESTER

(71) Applicant: SABIC BASIC INDUSTRIES CORPORATION, Riyadh (SA)

(72) Inventors: Syed Azhar Hashmi, Riyadh (SA); Flaiyh Al-Anazi, Riyadh (SA)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 14/350,596

(22) PCT Filed: Oct. 8, 2012

(86) PCT No.: PCT/EP2012/004205
§ 371 (c)(1),
(2) Date: Apr. 9, 2014

(87) PCT Pub. No.: WO2013/053455
PCT Pub. Date: Apr. 18, 2013

(65) Prior Publication Data
US 2014/0275604 A1 Sep. 18, 2014

(30) Foreign Application Priority Data
Oct. 11, 2011 (EP) ..................................... 11008210

(51) Int. Cl.
C07C 69/00 (2006.01)
C07C 67/08 (2006.01)
C07C 67/11 (2006.01)

(52) U.S. Cl.
CPC ................. *C07C 67/08* (2013.01); *C07C 67/11* (2013.01)

(58) Field of Classification Search
CPC ................................. C07C 69/92; C07C 67/08
See application file for complete search history.

(56) References Cited

U.S. PATENT DOCUMENTS 5,260,475 A 11/1993 Desmurs et al.
8,143,436 B2* 3/2012 Sainani ........................... 560/64

FOREIGN PATENT DOCUMENTS

| IN | 203929 B | 4/2005 |
| IN | 224081 | 6/2007 |
| JP | 58154537 | * 9/1983 |
| JP | 1294654 A | 11/1989 |
| WO | 2008138457 A1 | 11/2008 |

OTHER PUBLICATIONS

JP537 (JP 58154537 1983, all references to JP537 are to an English translation ).*
JP537 (JP 58154537 1983, all references to JP537 are to an English translation).*
Barry et al. 1985 "Solid-Liquid Phase-Transfer Catalysis Without Added Solvent. A Simple Efficient and Inexpensive Synthesis of Aromatic Carboxylic Esters by Alkylation of Potassium Carboxylates", Symthesis, Georg Thieme Verlag, Stuttgart, DE, Jan. 1, 1985, pp. 40-45.
JP58154537; Sep. 14, 1983; Abstract Only (1 page).
International Search Report and Written Opinion for PCT/EP2012/004205, International Filing Date Aug. 10, 2012, Date of Mailing Jan. 18, 2013, 16 pages.

* cited by examiner

*Primary Examiner* — Yevegeny Valenrod
*Assistant Examiner* — Blaine G Doletski
(74) *Attorney, Agent, or Firm* — Cantor Colburn LLP

(57) ABSTRACT

The invention relates to a process for preparing a compound represented by the formula 1 which compound may optionally be further mono- or di- substituted with halogen atoms, alkyl groups having 1 to 4 C— atoms and/or alkoxy groups having 1 to 4 C— atoms, wherein R is methyl or ethyl group, comprising the step of: contacting a corresponding compound represented by the formula 2 which compound is not further substituted or further mono- or di- substituted in corresponding positions with halogen atoms, alkyl groups having 1 to 4 C— atoms and/or alkoxy groups having a to 4 C-atoms, with an alkylating agent, wherein the alkylating agent is a compound of the formula $(RO)_2SO_2$ or RX, wherein R has the above meaning and X is halogen, in the presence of a bis-quaternary ammonium salt or a polymeric quaternary ammonium salt, in a two-phase system of an aqueous solution of a base and an organic solvent.

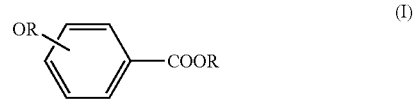

(I)

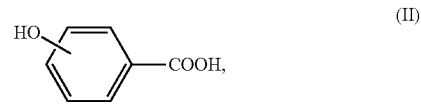

(II)

20 Claims, No Drawings

PROCESS FOR PREPARING ALKOXY ARYL ESTER

This application is a national stage application of PCT/EP2012/004205, filed Oct. 8, 2012, which claims priority from EP11008210.4 filed Oct. 11, 2011, both of which are hereby incorporated by reference in their entirety.

The present invention relates to a process for preparing alkoxy aryl esters. In particular, the present invention relates to a process for preparing a compound represented by the formula

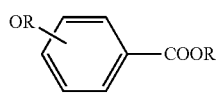

(I)

which compound may optionally be further mono- or di-substituted with halogen atoms, alkyl groups having 1 to 4 C— atoms and/or alkoxy groups having 1 to 4 C— atoms, wherein R is methyl or ethyl group.

Alkoxy aryl esters are important intermediates for the synthesis of a wide variety of medicinal or drug compounds. They are also used as electrons donors for the catalyst used in homo and copolymerization of olefins.

One example of the compound of formula (I) is para-ethoxyethyl benzoate. Traditionally para-ethoxyethyl benzoate has been obtained in a two step process from para-hydroxybenzoic acid. In this traditional process, para-hydroxybenzoic acid is first esterified with excess ethanol under acidic and dehydrating conditions. The hydroxyethyl benzoate obtained is then alkylated by alkyl halides or dialkyl sulphates either by in situ preparation of phenoxide ion (by reaction of para-hydroxyethyl benzoate with base) or preformed from an aqueous solution of base, as described in Morrison, R. T. et. al., Organic Chemistry 3rd edition p-556 (1975). The disadvantages of this method are that yield and selectivity are low and that the method requires longer time and multiple steps.

IN 2244081 discloses a two step process for preparing para-ethoxyethyl benzoate comprising i) reacting para-hydroxybenzoic acid with diethyl sulphate, sodium carbonate and a phase transfer catalyst in the presence of an aromatic organic solvent and ii) reacting the resultant product with an aliphatic acid or a phenol. The phase transfer catalyst is a mono-quaternary ammonium salt prepared in-situ. The reaction takes a relatively long time of 20 to 24 hours.

IN203929 describes a one-pot synthesis of para-ethoxyethyl benzoate. Etherification and esterification of para-hydroxy benzoic acid is achieved by treating para-hydroxybenzoic acid with diethyl sulphate in the presence of sodium carbonate, benzyl chloride and triethyl amine in an aromatic organic solvent like xylene under anhydrous reaction condition. A phase transfer catalyst is prepared in situ. The in-situ prepared phase transfer catalyst is a mono-quaternary ammonium salt. The reaction is performed at a relatively high temperature of 135° C.-140° C. for a relatively long time of 18 hours. Diethyl sulphate is quenched with acids and/or phenols before the process is completed.

WO2008138457 describes a one-step process for preparing alkoxy ary esters by reacting hydroxy benzoic acids with a compound of the formula $R_nX$, wherein R is an alkyl group having 1 to 6 C-atoms and X is an acid rest group having a valence n, wherein the organic solvent is an alkyl substituted aromatic hydrocarbon and the reaction is carried out at a pH of 8-10. In the example, p-ethoxy ethylbenzoate and p-methoxy methylbenzoate were prepared using xylene as the solvent.

There is a constant need in the industry for an improved process for preparing alkoxy aryl esters.

It is an objective of the present invention to provide a process for preparing alkoxy aryl esters which is efficient and economical.

Accordingly, the present invention provides process for preparing a compound represented by the formula

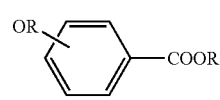

(I)

which compound may optionally be further mono- or di-substituted with halogen atoms, alkyl groups having 1 to 4 C— atoms and/or alkoxy groups having 1 to 4 C— atoms, wherein R is methyl or ethyl group, comprising the step of: contacting a corresponding compound represented by the formula

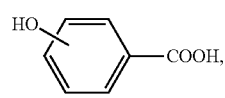

(II)

which compound is not further substituted or further mono- or di- substituted in corresponding positions with halogen atoms, alkyl groups having 1 to 4 C— atoms and/or alkoxy groups having a to 4 C-atoms, with an alkylating agent, wherein the alkylating agent is a compound of the formula $(RO)_2SO_2$ or RX, wherein R has the above meaning and X is halogen, in the presence of a bis-quaternary ammonium salt or a polymeric quaternary ammonium salt, in a two-phase system of an aqueous solution of a base and a liquid organic solvent.

According to the present invention, the use of the bis-quaternary ammonium salt or the polymeric quaternary ammonium salt allows a simultaneous process for etherification of OH group and esterification of COOH group. Such a one-pot one-step process is more efficient than two-step processes known from prior art. The process of the present invention offers cost saving on isolation and purification of the intermediate, and in eliminating unnecessary handling of chemicals and equipments. The alkoxy aryl ester is formed with ~100% selectivity and is easily separated from the solvent by distillation. Unlike with the process of IN203929, no quenching step is necessary.

Without the bis-quaternary ammonium salt or the polymeric quaternary ammonium salt, the reaction of the compound (II) and the alkylating agent is slow and incomplete, since the compound (II) has a tendency to remain in the aqueous phase and the alkylating agent has a tendency to remain in the organic phase. According to the present invention, the bis-quaternary ammonium salt or the polymeric quaternary ammonium salt acts as a phase transfer catalyst between the aqueous phase and the organic phase. The bis-quaternary ammonium salt or the polymeric quaternary ammonium salt was found to be an excellent agent for the transport of the anion of the compound (II) in the aqueous phase to the organic phase containing the alkylating agent. Bis-quaternary ammonium salts and the polymeric quaternary ammonium salts are more stable and more efficient than mono-quaternary ammonium salts. Mono-quaternary ammonium salts undergo decomposition in the presence of strong base.

The order of addition of the reaction components to the reaction system is not critical. For example, the alkylating agent may be added to the two-phase mixture of the compound (II), the aqueous solution of a base, the organic solvent and the bis-quaternary ammonium salt. The order of addition for making the two-phase mixture is not critical. For example, the compound (II) may be added to the aqueous solution of a base, followed by the organic solvent and subsequently the bis-quaternary ammonium salt. The addition of the compound (II) to the aqueous solution of a base is preferably performed slowly because of significant exothermic reaction. It is also possible that the compound (II) is added to the two-phase mixture of the aqueous solution of a base, the organic solvent, the alkylating agent and the bis-quaternary ammonium salt. Preferably, the bis-quaternary ammonium salt is added to the reaction system in the solid form or in the form of an aqueous solution.

The compound (II) is preferably not further substituted, i.e. the compound (II) is p-, m- or o-hydroxyl benzoic acid. In this case, the compound (I) is accordingly not further substituted.

The process according to the present invention has a further advantage that only a catalytic amount of the bis-quaternary ammonium salt or the polymeric quaternary ammonium salt is required. Preferably, the amount of the bis-quaternary ammonium salt or the polymeric quaternary ammonium salt is 0.5-10 mol % of the compound of formula (II), preferably 4-8 mol %, most preferably around 6 mol %.

The term "organic solvent" as used herein is very well known in the art. Accordingly, the term "organic solvent" relates to a liquid carbon-containing compound that is capable of dissolving a solute resulting in a solution. Preferably, the organic solvent is an apolar, aprotic organic solvent. It was found that apolar aprotic solvents are more suitable for a two phase system because of their lower dipole moment.

Preferably, the organic solvent is selected from the group consisting of ethylene dichloride, toluene and benzene, most preferably ethylene dichloride.

Preferably, the amount of the organic solvent is 10-50 wt % of the total of the compound (II), the alkylating agent, the bis-quaternary ammonium salt and the aqueous solution of a base.

The bis-quaternary ammonium salt may be chosen from a wide variety of salts. The bis-quaternary ammonium salt is generally represented by the following formula:

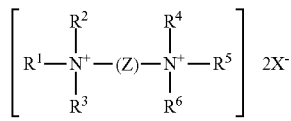

where $R^1$-$R^6$ are alkyl groups that may be alike or different, substituted or unsubstituted, saturated or unsaturated, branched or unbranched, and cyclic or acyclic and may contain ether, ester, or amide linkages, or they may be aromatic or substituted aromatic groups. The alkyl groups of $R^1$-$R^6$ may e.g. have 1 to 12 carbon atoms. $X^-$ is an anionic counterion. The term "anionic counterion" includes any ion that can form a salt with quaternary ammonium. Examples of suitable counterions include halides such as chlorides and bromides, propionates, carbonates, methosulphates, saccharinates, ethosulphates, hydroxides, acetates, phosphates, and nitrates.

Preferably, the anionic counterion is chloride. Z is a carbon-hydrogen chain attached to each quaternary nitrogen. Examples of the bis-quaternary ammonium salt include 1,6-bis[1-methyl-3-(2,2,6-trimethylcyclohexyl)-propyldimethyl ammonium chloride]-hexane or triclobisonium chloride (commercially available as Triburon), 1,10-bis(2-methyl-4-anninoquinolinium chloride)-decane (commercially available Dequadin or Sorot) or CDQ prepared by reaction of alkyl [C12, 40%; C14, 50%; C16, 10%] dimethylamine with dichloroethyl ether. Also, reaction of 1,4-dichloro-2-butene with 2 mol of alkyl-dimethylamines or hexamethylenetetramine results in another example of a suitable bis-quaternary ammonium salt.

The examples of suitable polymeric quaternary ammonium salts include polyionenes such as poly[oxyethylene (dimethyliminio)ethylene(di-methyliminio)ethylene dichloride], poly[N-3-dimethylammonio)propyl]N-[3-ethylneoxyethylenedimethylammonio)propyl]urea dichloride, and alpha-4-[1-tris(2-hydroxyethyle)ammonium chloride).

The alkylating agent may be diethylsulfate or dimethylsulfate, or $CH_3F$, $CH_3Cl$, $CH_3Br$, $CH_3I$, $C_2H_5F$, $C_2H_5Cl$, $C_2H_5Br$ or $C_2H_5I$. Preferably, the alkylating agent is diethylsulfate or dimethylsulfate. The number of alkyl groups present in the alkylating agent does not have to be substantially exceed the number of the OH group and COOH group in the compound of formula (II), i.e. stoichiometric amount of the alkylating agent may be used. Preferably, the number of alkyl groups present in the alkylating agent is 100% to 110% of the number of the OH group and COOH group in the compound of formula (II).

The base of the aqueous solution may be any hydroxide type base, such as alkali metal hydroxide or alkaline earth metal hydroxide, for example sodium hydroxide. Even more preferably, phase transfer type hydroxide base such as benzyltrimethyl ammonium hydroxide may also be used. This reduces the amount of the required bis-quaternary ammonium salt and further increases the rate of reaction.

The reaction conditions can vary appreciably depending upon the particular reactants employed. The reaction can be conducted over a broad temperature and pressure range. Preferred is atmospheric pressure.

Preferably, the contacting step is performed at a reaction temperature of 75-100° C., preferably 75-85° C., most preferably around 80° C. It is an advantage of the process of the present invention that the reaction can be performed in a relatively low temperature.

Preferably, the reactants are held at the reaction temperature for 4-8 hours, preferably 5-7 hours, most preferably around 6 hours. It is an advantage of the process of the present invention that the reaction can be performed in a relatively short time.

The reaction can occur in any container, which can contain the reaction mixture and allow the reaction to proceed. Preferred are normal stainless steel reactors. The reaction of the compound (II) and the alkylating agent involves no special difficulties, with the reacting ingredients being simply contacted in any suitable manner.

A variety of conventional methods including distillation, extraction, phase separation etc., can be utilized to recover the reaction product, unreacted starting material, catalyst, and solvent. Advantageously, the compound of formula (I) is isolated from the reaction mixture while allowing the bis-quaternary ammonium salt or the polymeric quaternary ammonium salt in the aqueous phase.

It is noted that the invention relates to all possible combinations of features described herein, particularly features recited in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The present invention is explained in more detail herein below referring to the following non-limiting examples.

EXAMPLE I

A 4-necked 500 mL round bottom flask was set up in a water bath. Mechanical stirring rod was attached in the central neck, a digital thermocouple inlet in the hind side neck, condenser in the front side neck, a dropping funnel in the right side neck.

An aqueous solution comprising 0.4 moles of sodium hydroxide was added to the flask, followed by 0.2 moles of p-hydroxybenzoic acid with stirring. To the flask was then added 1.9 moles of ethylene dichloride and 0.01 moles of 1,6-bis[1-methyl-3-(2,2,6-trimethylcyclohexyl)-propyldimethyl ammonium chloride]-hexane sold by trade name Triburon.

The reaction mixture was then heated to 80° C. and 0.4 moles of diethyl sulphate was added portion wise through the dropping funnel.

The reaction was completed within 6 hours with over 90% conversion of p-hydroxybenzoic acid.

The gas chromatography analysis for the sample after 6 hours of reaction is summarized in table 1. It shows the formation of desired product p-ethoxyethyl benzoate with almost 100% selectivity. There were no traces of intermediate product p-hydroxyethyl benzoate or C-alkylated products. The product was isolated by extracting with ethylene dichloride followed by distillation.

TABLE 1

GC Analytical Data

| Components | Retention Time (Minutes) | % Peak Area | % Conversion of PHBA | % Selectivity of PEEB |
|---|---|---|---|---|
| p-hydroxy benzoic acid | 3.5 | 13.0 | 87 | |
| Diethyl sulphate | 3.80 | 0.03 | | |
| p-ethoxy ethylbenzoate | 11.7 | 83.5 | | 100 |
| p-hydroxy ethylbenzoate | 11.0 | 0.0 | | |
| Unknown (PTC) | 16.0 | 3.5 | | |

Comparative Experiment A

The experiment was performed identically to example 1 except that the phase transfer catalyst was 0.05 moles of tetrabutylammonium chloride, which is a mono-quaternary ammonium salt. GC analysis showed 18% unreacted hydroxybenzoic acid and ~78% p-hydroxyethyl benzoate and 4% of other byproducts. Thus the reaction proceeded selectively at the COOH group. This comparison shows that not all phase transfer catalysts are suitable for simultaneous O-alkylation.

Comparative Experiment B

The experiment was performed identically to example 1 except that the phase transfer catalyst was not used. GC analysis showed 30% unreacted hydroxybenzoic acid and 60% p-hydroxyethyl benzoate, and 10% of diethyl sulphate. This shows that the reaction was not complete and it proceeded selectively at the COOH group. This comparison shows that suitable phase transfer catalysts is necessary for simultaneous O-alkylation of a hydroxy and carboxyl group.

The invention claimed is:

1. A process for preparing a compound represented by the formula

(I)

which compound may optionally be further mono- or di-substituted with halogen atoms, alkyl groups having 1 to 4 C— atoms and/or alkoxy groups having 1 to 4 C— atoms, wherein R is methyl or ethyl group, comprising:
contacting a corresponding compound represented by the formula

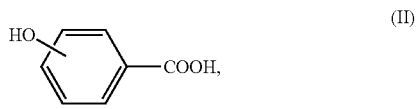

(II)

which compound is not further substituted or further mono- or di- substituted in corresponding positions with halogen atoms, alkyl groups having 1 to 4 C— atoms and/or alkoxy groups having a to 4 C— atoms, with an alkylating agent, wherein the alkylating agent is a compound of the formula $(RO)_2SO_2$ or RX, wherein R has the above meaning and X is halogen, in the presence of a bis-quaternary ammonium salt or a polymeric quaternary ammonium salt, in a two-phase system of an aqueous solution of a base and an organic solvent, solvent, wherein the polymeric quaternary ammonium salt is a polyionene.

2. The process according to claim 1, wherein the amount of the bis-quaternary ammonium salt or the polymeric quaternary ammonium salt is 0.5-10 mol % of the compound of formula (II).

3. The process according to claim 1, wherein the organic solvent is an apolar, aprotic organic solvent.

4. The process according to claim 3, wherein the organic solvent is selected from the group consisting of ethylene dichloride, toluene and benzene.

5. The process according to claim 1, wherein the amount of the organic solvent is 10-50 wt % of the total of the compound (II), the alkylating agent, the bis-quaternary ammonium salt or the polymeric quaternary ammonium salt, and the aqueous solution of a base.

6. The process according to claim 1, wherein the contacting is performed in the presence of the bis-quaternary ammonium salt, which is 1,6-bis[1-methyl-3-(2,2,6-trimethylcyclohexyl)-propyldimethyl ammonium chloride]-hexane.

7. The process according to claim 1, wherein the alkylating agent is diethylsulfate or dimethylsulfate.

8. The process according to claim 1, wherein the number of alkyl groups present in the alkylating agent is 100% to 110% of the number of the OH group and COOH group in the compound of formula (II).

9. The process according to claim 1, wherein the contacting is performed at a temperature of 75-100° C.

10. The process according to claim 9, wherein the reactants are held at the reaction temperature for 4-8 hours.

11. The process according to claim 1, wherein the compound of formula (I) is isolated from the reaction mixture while allowing the bis-quaternary ammonium salt or the polymeric quaternary ammonium salt to remain in the aqueous phase.

12. A process for preparing a compound represented by the formula

which compound may optionally be further mono- or di-substituted with halogen atoms, alkyl groups having 1 to 4 C— atoms and/or alkoxy groups having 1 to 4 C-atoms, wherein R is methyl or ethyl group, comprising contacting a corresponding compound represented by the formula

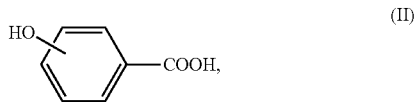

which compound is not further substituted or further mono- or di- substituted in corresponding positions with halogen atoms, alkyl groups having 1 to 4 C— atoms and/or alkoxy groups having a to 4 C-atoms, with an alkylating agent, wherein the alkylating agent is a compound of the formula $(RO)_2SO_2$ wherein R has the above meaning and wherein the number of alkyl groups present in the alkylating agent is 100% to 110% of the number of the OH group and COOH group in the compound of formula (II), in the presence of a bis-quaternary ammonium salt or a polymeric quaternary ammonium salt in an amount of 0.5-10 mol % of the compound of formula (II), in a two-phase system of an aqueous solution of a base and an apolar, aprotic organic solvent, wherein the amount of the organic solvent is 10-50 wt % of the total of the compound (II), the alkylating agent, the bis-quaternary ammonium salt or the polymeric quaternary ammonium salt, and the aqueous solution of a base.

13. The process according to claim 12, wherein the compound of formula (I) is para-ethoxyethyl benzoate and the compound of formula (II) is para-hydroxy benzoic acid.

14. The process according to claim 12, wherein the contacting is performed in the presence of the bis-quaternary ammonium salt, which is 1,6-bis[1-methyl-3-(2,2,6-trimethylcyclohexyl)-propyldimethyl ammonium chloride]-hexane.

15. The process according to claim 12, wherein the alkylating agent is diethylsulfate or dimethylsulfate.

16. The process according to claim 12, wherein the organic solvent is selected from the group consisting of ethylene dichloride, toluene and benzene.

17. The process according to claim 12, wherein
the contacting is performed at a temperature of 75-100° C., and
the reactants are held at the reaction temperature for 4-8 hours.

18. The process according to claim 12, wherein the compound of formula (I) is isolated from the reaction mixture while allowing the bis-quaternary ammonium salt or the polymeric quaternary ammonium salt to remain in the aqueous phase.

19. A process for preparing para-ethoxyethyl benzoate, comprising:
contacting para-hydroxy benzoic acid with an alkylating agent in the presence of a bis-quaternary ammonium salt or a polymeric quaternary ammonium salt, wherein the alkylating agent is a compound of the formula $(CH_3CH_2O)_2SO_2$ or $CH_3CH_2X$ wherein X is a halide, and wherein the polymeric quaternary ammonium salt is a polyionene.

20. The process according to claim 19, wherein the contacting is performed in the presence of the bis-quaternary ammonium salt, which is 1,6-bis[1-methyl-3-(2,2,6-trimethylcyclohexyl)-propyldimethyl ammonium chloride]-hexane.

* * * * *